United States Patent [19]

Nagato et al.

[11] 4,233,242

[45] Nov. 11, 1980

[54] PROCESS FOR PRODUCING KETAZINE BY REACTING A KETONE WITH AMMONIA AND A PEROXIDE

[75] Inventors: Nobuyuki Nagato, Wako; Yuichi Sugiyama, Tokyo, both of Japan

[73] Assignee: Showa Denko Kabushiki Kaisha, Tokyo, Japan

[21] Appl. No.: 27,895

[22] Filed: Apr. 6, 1979

[30] Foreign Application Priority Data

Apr. 13, 1978 [JP] Japan .................................. 53-42647
Apr. 13, 1978 [JP] Japan .................................. 53-42648

[51] Int. Cl.³ .................. C07C 109/12; C07C 109/14; C07C 109/16; C07C 119/00
[52] U.S. Cl. ..................................... 564/249; 252/449; 252/460
[58] Field of Search ..................................... 260/566 B

[56] References Cited

U.S. PATENT DOCUMENTS

| | | | |
|---|---|---|---|
| 3,892,805 | 7/1975 | Eichenhofer et al. | 260/566 B |
| 3,972,876 | 8/1976 | Schirmann et al. | 260/566 B |
| 3,972,878 | 8/1976 | Schirmann et al. | 260/566 B |
| 3,978,049 | 8/1976 | Schirmann et al. | 260/566 B |

Primary Examiner—Floyd D. Higel
Attorney, Agent, or Firm—Armstrong, Nikaido, Marmelstein & Kubovcik

[57] ABSTRACT

Ketazines having the general formula (I)

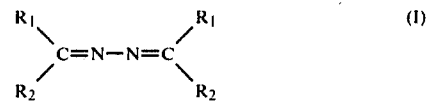

wherein $R_1$ represents alkyl group having 1 to 4 carbon atoms and $R_2$ represents (i) an alkyl group having 1 to 4 carbon atoms or (ii) a phenyl group optionally substituted with an alkyl group having 1 to 4 carbon atoms, an alkoxy group having 1 to 4 carbon atoms or a halogen group, and $R_1$ and $R_2$ together with the carbon atom to which they are both bonded may form a ring, are advantageously manufactured by reacting an aliphatic or aromatic ketone having the formula (II)

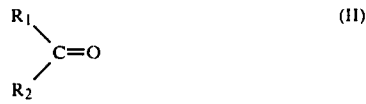

wherein $R_1$ and $R_2$ are as defined above, with ammonia and a peroxide compound or compounds in the presence of amorphous silica or palladium compounds, as a catalyst, at a temperature of from 0° to 120° C., in a liquid phase.

10 Claims, No Drawings

PROCESS FOR PRODUCING KETAZINE BY REACTING A KETONE WITH AMMONIA AND A PEROXIDE

The present invention relates to a process for producing ketazines. More specifically, it relates to a process for producing ketazines by reacting ketones with ammonia and a peroxide compound or compounds in the presence of, as a catalyst, silica or palladium compounds.

Recently, since synthetic processes of hydrazine via ketazines have been developed, various processes for producing ketazines have been proposed. Among those processes, processes using, as starting materials, ketones, ammonia and hydrogen peroxide are known in the art. For instance, U.S. Pat. Nos. 3,869,541, 3,943,152 and 3,972,876 disclose processes in which the starting materials are reacted with each other in the presence of nitriles or amides according to the following reaction sequences.

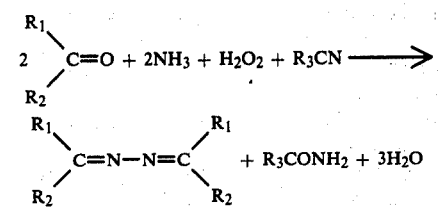

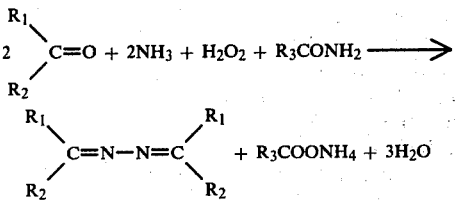

However, these processes present a substantial economic disadvantages in that nitriles or amides must be present in the reaction system and they are converted to the amides or the ammonium salts of the carboxylic acid of which separation, recovery and purification steps are troublesome and costly.

In addition, British patent specification No. 1,446,279 discloses the use of selenium and/or tellurium or compounds of these elements as a catalyst in order to prevent the use of the above-mentioned nitriles or amides. However, since selenium and tellurium which are used as a catalyst are toxic substances, there are still problems, from the industrial point of view, that the catalyst must be carefully handled and the waste water derived from the production step must be purified.

Accordingly, an object of the present invention is to obviate the above-mentioned disadvantages or problems of the prior processes and to provide an improved process for industrially advantageously producing a ketazine from ketone, ammonia and peroxide compounds.

In accordance with the present invention, there is provided a process for producing a ketazine having the general formula (I)

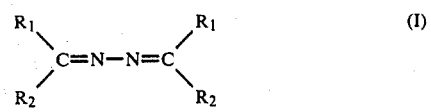

wherein $R_1$ represents alkyl group having 1 to 4 carbon atoms and $R_2$ represents (i) an alkyl group having 1 to 4 carbon atoms or (ii) a phenyl group optionally substituted with an alkyl group having 1 to 4 carbon atoms, an alkoxy group having 1 to 4 carbon atoms or a halogen group, and $R_1$ and $R_2$ together with the carbon atom to which they are both bonded may form a ring, which process comprises reacting an aliphatic or aromatic ketone having the formula (II)

wherein $R_1$ and $R_2$ are as defined above, with ammonia and a peroxide compound or compounds in the presence of silica, at least one palladium compound or a mixture thereof, as a catalyst, at a temperature of from 0° to 120° C., in a liquid phase. The ketazine (I) thus produced, after separation, can be reacted with water and/or an aqueous strong acid to form hydrazine hydrate and/or hydrazine salt and regenerate the starting ketone (II) according to the following reaction sequences.

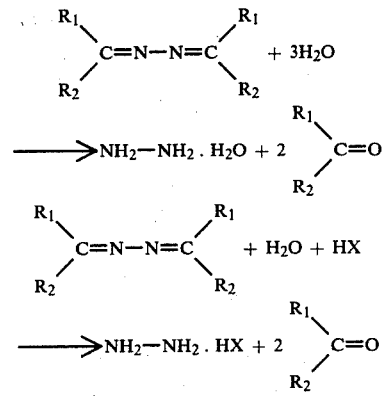

Thus, the regenerated ketone (II) can be used again as a starting material for the production of the azine (I). These production procedures of hydrazine from azines are known and described in, for example, U.S. Pat. No. 3,869,541 Japanese Patent Publication Nos. 44-14093(1969) and 49-48640(1974). Pertinent portions of the descriptions of these references are incorporated into the body of the present specification. The ketazine is also suitable for use in the production of pharmaceutical preparations, dyes, pesticides and the like.

The starting ketones employed in the present invention are represented by the above-general formula (II). Typical examples of such ketones are acetone, methyl ethyl ketone, methyl isobutyl ketone, cyclohexanone, acetophenone, methyl 3-methylphenyl ketone, methyl 4-methoxyphenyl ketone and methyl 3-chlorophenyl ketone. In the case where the present ketazine production process is carried out as one step for the production of hydrazine, ketones such as acetone, which are easily handled and readily available at low cost, can be preferably used from the point of easy operation and also economical point of view. This is because the produced ketazine is hydrolyzed to form hydrazine and, as a by-product, the starting ketone, and the ketone is recovered.

The typical peroxide compound employed in the preferable embodiment of the present invention is hydrogen peroxide. However, other peroxide compounds can also be used as a peroxide compound in the present invention; such as, for example, a liquid phase oxidation reaction product of secondary alcohol (e.g. isopropanol, sec. butanol, cyclohexanol and 1-phenyl ethanol) with oxygen including an oxygen containing gas such as air; a reaction product of the ketone $R_1COR_2$ and hydrogen peroxide; a reaction product of the ketone $R_1COR_2$, hydrogen peroxide and ammonia. The ketone used in the above two reactions for preparing peroxide compounds can be preferably that which is used as a starting material for the ketazine production. Typical examples of the above-mentioned peroxide compounds are hydroxy hydroperoxides and amino hydroperoxides having the following formula (III),

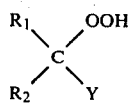
(III)

wherein $R_1$ and $R_2$ are as defined above and Y represents OH or $NH_2$, as well as any secondary reaction products thereof and having, for example, the following formulae (IV), (V) and (VI).

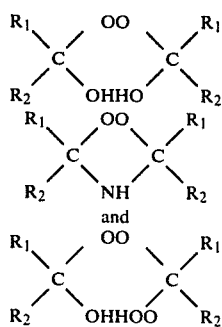

wherein $R_1$ and $R_2$ are as defined above.

These peroxide compounds and the reaction mechanism thereof are well known and are described in, for example, EUROPEAN CHEMICAL NEWS, page 27 (Jan. 24, 1969); HYDROCARBON PROCESSING 44, No. 7, 116(1965); J.A.C.S. 77 1756(1955); J.C.S. 1180(1952); J.A.C.S. 61, 2430(1939); CHEMICAL ABSTRACT 71, 10143e(1969); and; J. Chem. Soc. (c) 2663(1969). The pertinent descriptions of these references are incorporated into the body of the present specification. Other known syntheses can be also utilized for the production of the peroxide compounds.

These peroxide compounds including hydrogen peroxide can be used alone or any mixture thereof. The hydrogen peroxide can be used in an aqueous or non-aqueous solution of any concentration. In the case where an aqueous hydrogen peroxide solution is used, the preferable concentration of hydrogen peroxide in the solution is within the range of from 10 to 90% by weight. In the case where the above-mentioned peroxide compounds are used, preferable concentration of the peroxide compounds in the solution is within the range of from 0.3 to 40% by weight, in terms of hydrogen peroxide. These reaction products can be used directly or after dilution or concentration. Examples of suitable non-aqueous solvents are alcohols, esters, ethers, hydrocarbons and halogenated hydrocarbons.

The ammonia employed in the present invention can be in liquid, gaseous or dissolved form. In the case where an aqueous ammonia solution is used, the preferable concentration of ammonia in the solution is within the range of from 5 to 28% by weight.

The catalyst employed in the present invention includes silica, especially amorphous silica and palladium compounds, especially palladium (II) compounds and any mixture thereof.

By the term "amorphous silica" used in this specification is meant substantially dehydrated, polymerized silica which may be considered as a condensation polymer of silicic acid. Typical amorphous silica which can be used in the present invention includes silica gel, precipitated silica, fumed silica or the like. Amorphous silica which is conventionally used as a desiccant, an adsorbent, a catalyst, a catalyst carrier, a filler or the like can be utilized without any special treatment in the reaction according to the present invention. Amorphous silica in any forms such as beads, granules, crushed particles, powders and the like can be used in the present invention.

In the case where amorphous silica is used as the catalyst, since better results are obtained when the amount of water present in the reaction medium is small, the inventors of the present invention prefer to use non-aqueous peroxide compounds. For this reason, the direct use of the liquid-phase oxidation reaction mixture of a secondary alcohol as the peroxide compound results in the practical advantage that only slight amounts of water, which are formed as a by-product during the liquid-phase oxidation of the secondary alcohol, are incorporated into the reaction system. Especially, when a secondary alcohol corresponding to the starting ketone for the production of ketazine is used, all components contained in the liquid-phase oxidation reaction mixture of the secondary alcohol are effectively useful for the production of the ketazine. For instance, when acetone-azine is prepared from acetone, the oxidation reaction mixture of isopropanol is effectively used as the peroxide compound. That is, the oxidation reaction mixture of isopropanol contains the unreacted isopropanol, the desired peroxides such as hydrogen peroxide, 2-hydroxyisopropyl hydroperoxide, and the like, as well as acetone. Since these components are the solvent and starting materials of the present process, respectively, and since the reaction mixture is substantially non-aqueous, the desired reaction effectively proceeds by the addition of the catalyst, ammonia and additional acetone.

Although the amount of the amorphous silica to be used as a catalyst is not critical in the process according to the present invention, the preferable amount of the amorphous silica is generally within the range of from 2 to 50% by weight, and more preferably within the range of from 5 to 30% by weight, based upon the total weight of the reaction mixture. When the amount of the amorphous silica catalyst is too small, the reaction rate becomes so slow that it is not practically preferable, and, also, since the catalytic activity of the amorphous silica is somewhat affected by the presence of water in the reaction mixture, the reaction rate is liable to further unpreferably decrease with the increase of the amount of water in the reaction mixture. Contrary to this, even if the amount of the amorphous silica is too large, further increase in the reaction rate can not be expected and, also, the economical burden, including the costs for separating and recovering the amorphous silica from the reaction mixture, unpreferably increases.

Any palladium (II) compounds, such as those in the form of the inorganic acid, organic acid or complex salt, can be used, as a catalyst, in the process according to the present invention. Examples of such palladium (II) compounds are palladium chloride, palladium fluoride, palladium bromide, palladium nitrate, palladium sulfate, palladium cyanide, palladium oxychloride, palladium acetate, palladium propionate, palladium oxalate, palladium dipyridyl chloride, palladium dipyridyl nitrate, sodium palladium chloride, potassium palladium chloride, palladium acetylacetonate and palladium (II)-1.4-naphthoquino-5-oleate.

Although the amount of the palladium compound to be used as a catalyst is not critical in the process according to the present invention, the preferable amount of the palladium catalyst is generally within the range of from 0.001 to 5.0 m mol, and more preferably within the range of from 0.005 to 0.5 m mol, based upon 1 g of the reaction mixture. When the amount of the palladium catalyst is too small, the reaction rate tends to become slow and, therefore, it is not practically preferable. On the other hand, when the amount of the palladium catalyst is too large, there is some danger that the starting peroxide compound may be decomposed and, also, the economical burden unpreferably increases.

The palladium (II) compounds used in the present invention are not necessarily those which are of highly purity, and palladium (II) compounds available from the commercial market can be used without any purification. Occasionally, palladium compounds containing impurities which decompose the peroxide compound decrease the expected yield of the desired ketazine. However, the inventors of the present invention have found that, when the palladium compound containing such impurities is previously treated with silica gel, a remarkably higher yield of the desired ketazine can be obtained in comparison with the non-treated palladium compound. For example, the treatment of palladium compounds with silica gel can be carried out as follows. The palladium compound to be treated is first dissolved in a suitable solvent or in a portion of the starting reactant and silica gel is then added into the solution. The mixture so formed is agitated for about 30 minutes and then filtered. The mother liquor thus obtained can be used in the process according to the present invention. Alternatively, the solution containing the palladium compound dissolved therein can be treated by passing it through a column provided with silica gel packing layer.

Although the ratio of the ketone, ammonia and peroxide compound is normally stoichiometric (i.e. 2:2:1 in a mol ratio) in the process according to the present invention, one or two of these three reactants can be used in amounts in excess of or less than the stoichiometric ratio. However, in view of the ketazine yield, and also from an economical point of view, the inventors of the present invention prefer to use 0.5 through 35 mol, and more preferably 1.4 through 10 mol, of the ketone and not less than 1 mol, and more preferably 2 through 20 mol, of ammonia, based upon 1 mol of the peroxide compound in the process according to the present invention. In addition, these reactants can be totally mixed prior to the reaction, or any reactant or a portion thereof can be additionally charged into the reaction mixture after the reaction starts up.

In addition to the catalyst, stabilizers which can prevent the possible decomposition of the peroxide compound can be effectively incorporated into the reaction system, especially when the reaction temperature is too high or there is some danger that the peroxide compound will be decomposed due to the presence of impurities contained in the starting materials or the catalyst. Examples of such stabilizers are polycarboxy derivatives of ammonia or alkylene polyamine, such as, for example, iminodiacetic acid, iminodipropionic acid, nitrilotriacetic acid, ethylenediamine diacetic acid, ethylenediamine tetraacetic acid, ethylenediaminedipropionic acid, hydroxyethylenediamine triacetic acid, diethylenetriamine triacetic acid, diethylenetriamine tetraacetic acid, diethylenetriamine pentaacetic acid and the alkali metal salts thereof; as well as phosphoric acid, pyrophosphoric acid and the alkali or ammonium salts thereof. Although the amount of the stabilizer, if it is used in the present invention, may be varied over a wide range, the suitable amount of the stabilizer to be used in the process according to the present invention is less than about 4% by weight of the reaction mixture. This is because, if an excessive amount of the stabilizer is used, the decomposition of the peroxide compound will be liable to occur in the case of an aqueous reaction medium, and also, in the case of non-equeous reaction medium the stabilizer can not be dissolved in the reaction mixture in view of its solubility.

Since the ketone, ammonia and proxide compound can be reacted with each other by the presence of the catalyst, the process according to the present invention can be carried out in the absence of solvents. However, in order to obtain a desired product in a satisfactory yield, from a practical point of view, the process according to the present invention is preferably carried out in the presence of any suitable solvent. Any solvents which are stable and do not decompose the starting materials and the reaction products, under the reaction conditions can be used in the present process. Examples of such solvents are water, alcohols, esters, ethers, hydrocarbons, halogenated hydrocarbons, sulfones and the like. For a practical use, preferable solvents are those which can dissolve the starting materials to a great extent and which can be easily separated from the reaction mixture, and also, which are readily available at a low cost.

The process according to the present invention is generally carried out at a temperature of from 0° to 120° C., and more preferably from an ambient temperature to 100° C., at atmospheric pressure or an elevated pressure.

The present invention will now be further illustrated by, but is by no means limited to, the following Examples, in which the yields of ketazine are calculated by mol %, in terms of hydrogen peroxide, based upon the amount of the charged peroxide compounds.

EXAMPLE 1

Into a 300 ml flask, 180 ml of isopropanol, 40 g of powdered silica gel for a desiccant (SiO$_2$ content in dry base: 99.7% by weight, surface area: 720 m$^2$/g), 0.05 g of disodium ethylenediamine tetraacetate (i.e. EDTA 2Na) and 3.78 g (0.1 mol) of 90% aqueous hydrogen peroxide were added, and then, gaseous ammonia was introduced to the stirred resultant mixture at a rate of 750 ml/min, in a bath, at 60° C., while 8 g of acetone was added just after the beginning of the introduction of the ammonia. Five minutes after the beginning of the introduction of the ammonia, the rate of the ammonia introduction was reduced to 25 ml/min and the reaction was continued for 8 hours. During this reaction period 1 g each of acetone was additionally added to the reaction mixture at 30 minutes, 1 hour, 2 hours, 3 hours, 4 hours and 6 hours after the beginning of the reaction. After the completion of the reaction, 7.28 g of acetone-azine, which was determined by gas chromatography, was formed. This corresponds to a 65% yield based upon the charged hydrogen peroxide.

The reaction mixture was filtered, to thereby remove silica gel, and the solvent and others were distilled off from the filtrate. Acetone-azine thus obtained was separated, by distillation, from the resultant liquid.

Into 10 g of 35% by weight of an aqueous acetone-azine solution which was prepared from the acetone-azine obtained above, 5.9 g of concentrated sulfuric acid was dropwise added at a temperature of 25° C., to thereby form the precipitation of monohydrazine sulfate. The precipitation was filtered, washed with a small amount of cold water and dried. Thus, 4.0 g of monohydrazine sulfate was obtained.

EXAMPLE 2

Into a 25 ml flask, 2 g of high purity silica gel for thin-layer chromatography (Fe content 0.002%, Cu content 0.0005%, Pb content 0.0005%), and 0.02 g of EDTA 2Na were charged, and then, 12 ml of methanol and 0.75 g (20.3 m mol) of about 90% aqueous hydrogen peroxide were added, and further, 1 ml of a 1/1 (vol/vol) of methanol/acetone mixture saturated with ammonia therein was added. Gaseous ammonia was introduced in a small stream into the stirred resultant mixture in an oil bath, at a temperature of 60° C. 1 ml each of the above-mentioned methanol/acetone mixture was additionally charged to the reaction mixture at 30 minutes, 1 hour, 2 hours, 4 hours and 6 hours after the beginning of the reaction. Eight hours after the beginning of the reaction, acetone-azine, which was determined by gas chromatography, was obtained with a yield of 46.6% (which corresponds to 70.7% based upon the reacted hydrogen peroxide).

EXAMPLE 3

2 g of silica gel for column chromatography, which were passed through a sieve having a size of 325 mesh, and 0.02 g of EDTA 2Na were charged into a flask, and then, 12 ml of methanol, 0.75 g (20.3 m mol) of about 90% aqueous hydrogen perxide and 3 ml of acetone were added. After gaseous ammonia was bubbled into the mixture contained in the flask, to thereby saturate the mixture with ammonia, ammonia gas was introduced in a small stream into the vigorously stirred resultant mixture, in a bath, at a temperature of 60° C. The reaction was continued for 8 hours. Acetone-azine, which was determined by gas chromatography, was obtained with a yield of 48.9%.

EXAMPLE 4

The reaction was carried out in a manner similar to that described in Example 2, except that 5 g of the silica gel used in Example 3 was used. After 8 hours reaction, acetone-azine, which was determined by gas chromatography, was obtained with a yield of 62.6% (which corresponds to 70.5%, based upon the reacted hydrogen peroxide).

EXAMPLE 5

The reaction was carried out in a manner similar to that described in Example 2, except that 2 g of silica gel for column chromatography, having a size of 100 through 200 mesh (manufactured by WAKO PURE CHEMICAL IND., LTD.), and 0.2 g of EDTA 2Na were used. After the completion of the reaction, acetone-azine was formed with a yield of 32.3%.

EXAMPLE 6

2 g of silica aerogel (manufactured by NIPPON AEROSIL CO., LTD.), 0.4 g of EDTA 4Na and 33 ml of methanol were charged into a flask. Into the mixture, 0.75 g (20.3 m mol) of about 90% aqueous hydrogen peroxide and 2 ml of the mixed solution of methanol, acetone and ammonia used in Example 2 were added. The reaction was carried out for 6 hours at a temperature of 60° C., while 2 ml each of the mixed solution of methanol, acetone and ammonia were additionally charged four times. Acetone-azine was obtained with a yield of 15.3%.

EXAMPLE 7

The reaction was carried out in a manner similar to that described in Example 2 for 6 hours, except that 2 g of silica gel powder, which was prepared by grinding silica gel for a desiccant in granular form in a mortar, were used. The yield of the acetone-azine was 44.5% (which corresponds to 72.1%, based upon the reacted hydrogen peroxide).

EXAMPLE 8

The reaction was carried out in a manner similar to that described in Example 3, except that 2 g of silica gel used in Example 5 and, instead of about 90% aqueous hydrogen peroxide, 2 ml (20.2 m mol) of about 30% aqueous hydrogen peroxide were used. After the completion of 8 hours reaction, acetone-azine was obtained with a yield of 20.7%.

EXAMPLE 9

The reaction was carried out in a manner silimar to that described in Example 8, except that 2 g of the silica gel used in Example 3 was used. At 6 hours after the beginning of the reaction, acetone-azine was obtained with a yield of 25.1%.

EXAMPLE 10

The reaction was carried out, in a manner similar to that described in Example 3, by using 2 g of the silica gel used in Example 5, 0.2 g of disodium phosphate, 10 ml of methanol, 5 ml of acetone and 2 ml (20.2 m mol) of about 30% aqueous hydrogen peroxide. Eight hours after the beginning of the reaction, acetone-azine was obtained with a yield of 18.8%.

EXAMPLES 11 TO 15

The following Examples were carried out by using various solvents. In Examples 11, 12 and 13, the reactions were carried out using a reaction procedure and conditions similar to those described in Example 2. In Examples 14 and 15, the reactions were carried out in a manner similar to that described in Example 3, except that the silica gel used in Example 2 was used. The results are shown in Table 1.

TABLE 1

| Ex. No. | Solvent | Reaction Time(hr) | Ketazine Yield(%) |
|---|---|---|---|
| 11 | Isopropanol | 8 | 45.1 |
| 12 | 1-Phenyl Ethanol | 8 | 38.9 |
| 13 | 2,4-Dimethyl Sulfolane | 6 | 34.1 |
| 14 | Benzene | 6 | 28.3 |
| 15 | Ethyl Acetate | 8 | 65.3 |

EXAMPLE 16

The reaction was carried out with vigorous stirring, in a bath, at a temperature of 60° C., while into a mixture of 2 g of the silica gel used in Example 2, 0.02 g of EDTA.2Na, 15 ml of acetone and 20.3 m mol of about 90% aqueous hydrogen peroxide, gaseous ammonia was introduced. At 6 hours after the beginning of the reaction, acetone-azine was obtained with a yield of 7.2%.

EXAMPLE 17

The reaction was carried out in a manner similar to that described in Example 3, except that 2 g of the silica gel used in Example 5 was used and the reaction temperature was 40° C. At 6 hours after the beginning of the reaction, acetone-azine was obtained with a yield of 7.2%.

EXAMPLE 18

The reaction was carried out in a manner similar to that described in Example 3, except that 2 g of the silica gel used in Example 2 was used and the reaction temperature was room temperature. Eight hours after the beginning of the reaction, acetone-azine was obtained with a yield of 2.2%.

EXAMPLE 19

The reaction was carried out with vigorous stirring, in a bath, at a temperature of 60° C., while gaseous ammonia was introduced in a very small stream into a mixture of 2 g of the silica gel used in Example 5, 15 ml of methanol and 8 m mol of 1,1'-peroxy-diisopropyl amine (which was prepared from acetone, ammonia and hydrogen peroxide and isolated from the reaction mixture by distillation). Six hours after the beginning of the reaction, acetone-azine was obtained with a yield of 42.0%.

EXAMPLE 20

To the silica gel used in Example 5, 12 ml of methanol, 5 ml of acetone and 20.3 m mol of about 90% aqueous hydrogen peroxide was added, and then, the resultant mixture was saturated with gaseous ammonia. The reaction was carried out with stirring at a temperature of 60° C., while gaseous ammonia was introduced, in a very small stream, into the mixture. Six hours after the beginning of the reaction, acetone-azine was obtained with a yield of 21.2%.

EXAMPLE 21

The reaction was carried out in a manner similar to that described in Example 20, except that about 30% aqueous hydrogen peroxide was used. and that 8 ml of acetone and 10 ml of methanol were used. Eight hours after the beginning of the reaction, acetone-azine was obtained with a yield of 15.6%.

EXAMPLE 22

The reaction was carried out in a manner similar to that described in Example 2, except that 2 g of silica gel (which was prepared by calcining the silica gel used in Example 5 for 2 hours, at a temperature of 600° C.) was used, and, also, that EDTA 2Na was omitted. The reaction was carried out for 8 hours. The yield of the acetone-azine thus obtained was 34.5%.

EXAMPLE 23

After the reaction mixture of Example 22 was allowed to stand for one night, the silica gel was recovered by filtration and washed with methanol one. By using the silica gel thus recovered, the reaction was carried our in a manner similar to that described in Example 2. The reaction was carried out for 8 hours. The yield of the azine thus produced was 21.6%. Although similar operations were repeated a further 9 times, substantially equal yields were obtained.

EXAMPLES 24 TO 27

By using various ketones, the following Examples were carried out. The amounts of methanol (solvent), hydrogen peroxide and EDTA 2Na used were the same as in Example 3. The results are shown in Table 2.

TABLE 2

| Ex. No. | Ketone | Reaction Temp.(°C.) | Reaction Time(hr) | Ketazine Yield(%) |
|---|---|---|---|---|
| 24 | Methyl Ethyl Ketone | 60 | 8 | 47.5 |
| 25 | Methyl Isobutyl Ketone | 65 | 12 | 33.0 |
| 26 | Cyclohexanone | 65 | 12 | 24.4 |
| 27 | Acetophenone | 65 | 12 | 8.6 |

EXAMPLE 28

The reaction was carried out by moderately introducing gaseous ammonia, with stirring, into a mixture of 4 g of the silica gel used in Example 2, 20 g of cyclohexanol, 8.8 g of cyclohexanone, 3.0 g of about 30% aqueous hydrogen peroxide and 0.04 g of EDTA.2Na, at a temperature of 60° C., for 6 hours. Cyclohexanone-azine, which was determined by gas chromatography, was obtained with a yield of 16.6%.

EXAMPLE 29

The reaction was carried out by moderately introducing gaseous ammonia, with stirring, into a mixture of 30 g of the reaction mixture (which was prepared by oxidizing cyclohexanol with oxygen and which contained 0.995 m mol/g of peroxide compounds), 8.8 g of cyclohexanone, 0.04 g of EDTA 2Na and 4 g of the silica gel used in Example 2, for 6 hours, at a temperature of 60° C. The yield of the cyclohexanone-azine thus produced was 27.7%.

EXAMPLE 30

The reaction was carried out by moderately introducing gaseous ammonia, with stirring, into a mixture of 17.0 g of the reaction mixture (which was prepared by oxidizing 1-phenyl ethanol with oxygen and which contained 1.263 m mol/g of peroxide compounds), 2 g of acetophenone, 0.02 g of EDTA.2Na and 2 g of the silica gel used in Example 2, for 6 hours, at a temperature of 120° C. The yield of the acetophenone-azine thus produced was 3.9%.

EXAMPLE 31

Isopropyl alcohol was oxidized with oxygen and the resultant reaction mixture was concentrated under reduced pressure. 2.34 g of this concentrated liquid containing the peroxides (the concentration of the peroxides were 4.11 m mol/g) was dissolved in 10 ml of methanol, and further, 2 g of the silica gel used in Example 3 and 0.02 g of EDTA.2Na were added thereto. After 1 ml of the mixture of methanol, acetone and ammonia, obtained in a manner similar to that described in Example 2, was added to the resultant mixture, the reaction was carried out by introducing, with stirring, gaseous ammonia into the reaction mixture, at a temperature of 60° C. 1 ml each of the above-mentioned mixture of methanol, acetone and ammonia was additionally charged at 30 minutes, 1 hour, 2 hours and 4 hours after the beginning of the reaction. The reaction was carried out for a further 4 hours and was stopped at 8 hours, in total, after the beginning of the reaction. Acetone-azine, which was determined by analysis, was thus obtained with a yield of 62.6%. This yield corresponds to 69.4%, based upon the consumed peroxide.

EXAMPLE 32

Into 12.4 g of the reaction mixture containing peroxides which was obtained by oxydizing isopropyl alcohol with oxygen (the concentration of the peroxides was 1,533 m mol/g), 0.02 g of EDTA 2Na, 2 g of the silica gel used in Example 1 and 0.5 ml of acetone were added. The reaction was carried out by moderately introducing gaseous ammonia, with stirring, into the reaction mixture, at a temperature of 60° C. At 30 minutes, 1 hour, 2 hours, 4 hours and 6 hours after the beginning of the reaction, 0.5 ml each of acetone was additionally charged. At 8 hours after the beginning of the reaction, the acetone-azine, which was determined by analysis, was obtained with a yield of 55.4%, which corresponds to 69.0%, based upon the consumed peroxide.

EXAMPLE 33

2.24 g of palladium acetate and 0.520 g of EDTA.4Na were dissolved in 36 g of 25% aqueous ammonia and, then, 15.8 g of acetone was added thereto. 5.54 g of 30.5% aqueous hydrogen peroxide was very slowly introduced into this solution, over 7.5 hours, at a temperature of 33° C. After 26 hours, acetone-azine, which was determined by gas chromatography, was formed with a yield of 75.8%.

EXAMPLES 34 TO 37

2.24 g of palladium acetate and 0.520 g EDTA.4Na were dissolved in 36 g of 25% aqueous ammonia, and then, the ketone and the methanol listed in Table 3 below were added. The mixture was heated to a temperature of 50° C., with stirring. 5.54 g of 30.5% aqueous hydrogen peroxide were slowly introduced into this solution over 3 hours, and the reaction was carried out for a further 15 hours. The corresponding ketazine was obtained as a shown in Table 3.

TABLE 3

| Ex. No. | Ketone | Methanol | Ketazine Yield (%) |
|---|---|---|---|
| 34 | Methyl Ethyl Ketone (20 ml) | 10 ml | 40.3 |
| 35 | Methyl Isobutyl Ketone (20 ml) | 40 ml | 8.2 |
| 36 | Cyclohexanone (20 ml) | 20 ml | 23.1 |
| 37 | Acetophenone (20 ml) | 60 ml | 3.7 |

EXAMPLE 38

Acetone-azine was prepared by using a peroxide solution which was obtained by oxydizing isopropanol with air. 4.76 g of the peroxide solution (containing 8.09 m mol of peroxides in terms of hydrogen peroxide) was added to a solution of 2.24 g of palladium acetate, 0.520 g of EDTA.4Na and 7.90 g of acetone dissolved in 18 g of 25% aqueous ammonia, and reacted for 4 hours, at a temperature of 44° C. Acetone-azine was obtained with a yield of 80.6%.

EXAMPLE 39

1.31 g of 3,3,5,5-tetramethyl dioxazolane (78.3% by weight of acetone solution) was added to a solution of 0.56 g of palladium acetate, 0.130 g of EDTA.4Na and 3.95 g of acetone dissolved in 5 g of 25% aqueous ammonia. The resultant mixture was allowed to react at a temperature of 39° C., for 2 days. Acetone-azine was obtained with a yield of 36.3%.

EXAMPLES 40 TO 43

The palladium salt listed in Table 4 below was added to 4.05 g of 25% aqueous ammonia and, thereinto, 15.8 g of acetone and 0.52 g of EDTA.4Na were dissolved. Gaseous ammonia was slowly introduced into the reaction mixture, with stirring, at a temperature of 50° C. The reaction was carried out by dropwise adding 5.54 g of 30.5% aqueous hydrogen peroxide over 3 hours and was continued for a further 21 hours. Thus, acetone-azine was produced. The results are shown in Table 4.

TABLE 4

| Ex. No. | Palladium Salt | Acetone-Azine Yield (%) |
|---|---|---|
| 40 | Palladium Chloride (1.77 g) | 12.0 |
| 41 | Palladium Nitrate (1.0 g) | 21.3 |
| 42 | Palladium Sulfate (1.0 g) | 15.0 |
| 43 | Palladium Cyanide (2.0 g) | 8.6 |

EXAMPLES 44 TO 46

Palladium acetate and EDTA.4Na were dissolved in 36 g of 25% aqueous ammonia in amounts shown in Table 5 below and, then, 15.8 g of acetone was added. The mixture was warmed on an oil bath and the reaction was carried out by adding 5.54 g of 30.5% aqueous hydrogen peroxide. Thus, acetone-azine was obtained. The results are shown in Table 5.

TABLE 5

| Example No. | 44 | 45 | 46 |
|---|---|---|---|
| Palladium Acetate | 70 mg | 4.48 g | 6.72 g |
| EDTA . 4Na | 16.3 mg | 1.04 g | 1.04 g |
| Reaction Temperature (°C.) | 44 | 33 | 37 |
| Dropwise Addition Time (hr) of Aqueous Hydrogen Peroxide | 3 | 7.5 | — |
| Reaction Time (hr) | 9 | 11.5 | 7 |
| Acetone-Azine Yield (%) | 4.24 | 57.2 | 66.6 |

EXAMPLES 47 TO 50

1.12 g of palladium acetate was dissolved in 36 g of 25% aqueous ammonia. In Example 47 and 48, into the solution thus obtained, 15.8 g of acetone and 5.54 g of 30.5% aqueous hydrogen peroxide (and 5 m mol of EDTA.4Na only in Example 48) were added, and the reaction was carried out for 10 hours, at a temperature of 50° C. In Example 49 and 50, the above-mentioned reaction was repeated, except that the palladium acetate solution was treated by silica gel before the beginning of the reaction. The treatment was carried out in such a manner that the silica gel was added to the solution and the mixture was agitated for 30 minutes, followed by filtering off the silica gel. In Example 50, 5 m mol of EDTA.4Na was also added to the reactant mixture. The results are shown in Table 6.

TABLE 6

| Ex. No. | Amount of EDTA . 4Na used | Amount of Silica Gel used | Acetone-Azine Yield (%) |
|---|---|---|---|
| 47 | — | — | 10.0 |
| 48 | 5 m mol | — | 42.0 |
| 49 | — | 0.4 g | 49.6 |
| 50 | 5 m mol | 0.1 g | 57.1 |

EXAMPLES 51 TO 55

Palladium acetate, in an amount listed in Table 7 below, was dissolved in 36 g of 25% aqueous ammonia and then, the polycarboxy derivative of ammonia or alkylene polyamine as listed in Table 7 was added. The reaction was carried out, by adding 15.8 g of acetone and 5.54 g of 30.5% aqueous hydrogen peroxide, under the reaction conditions shown in Table 7. The yields of the acetone-azine thus obtained are also shown in Table 7.

TABLE 7

| Ex. No. | Polycarboxy Derivative of Ammonia or Alkylene Polyamine | Amount of Palladium Acetate used (g) | Reaction Time (hr) | Reaction Temp. (°C.) | Azine Yield (%) |
|---|---|---|---|---|---|
| 51 | — | 6.72 | 7.5 | 37 | 21.8 |
| 52 | EDTA . 4Na (1.04 g) | 2.24 | 10 | 50 | 59.1 |
| 53 | Nitrilotriacetic Acid (0.239 g) | 2.24 | 8 | 46 | 40.2 |
| 54 | Ethylenediamine Dipropionic Acid (0.346 g) | 2.24 | 8 | 46 | 37.4 |
| 55 | Trisodium Hydroxyethyl-ethylenediamine Triacetate (0.348 g) | 2.24 | 8 | 46 | 51.3 |

EXAMPLE 56

2.24 g of palladium acetate and 0.52 g of EDTA.4Na were dissolved in 36 g of 25% by weight of aqueous ammonia and, then, 4 g of acetone was added. The reactant mixture was heated to 50° C. and, then, 5.54 g of 30.5% aqueous hydrogen peroxide was dropwise added over 3 hours, while gaseous ammonia was introduced to the mixture. The reaction was continued for a further 6 hours. The yield of the acetone-azine thus obtained was 10.0%.

EXAMPLE 57

The reaction was carried out in a manner similar to that described in Example 49, except that 100 g of acetone was used, and also, the reaction period was 72 hours. The yield of the acetone-azine thus obtained was 33.1%.

EXAMPLE 58

This Example demonstrates the fact that a similar yield of acetone-azine can be obtained by again using the recovered aqueous palladium acetate solution from the reaction mixture after the acetone-azine was extracted with organic solvent.

PREPARATION OF AQUEOUS PALLADIUM ACETATE 4.48 g of palladium acetate and 1.04 g of EDTA.4Na were dissolved in 36 g of 25% aqueous ammonia. This solution was used for the first run and, thereafter, the recovered palladium acetate solutions from the reaction mixture were used in further runs.

SYNTHESIS OF ACETONE-AZINE

Into the above-mentioned aqueous palladium acetate solution, 15.8 g of acetone and 40 ml of benzene were added, and the mixture was heated to a temperature of 45° C. Gaseous ammonia was moderately introduced into the mixture with stirring. 5.54 g of 30.5% aqueous hydrogen peroxide was dropwise added over 3 hours and the reaction was further continued. After 8 hours, the benzene layer was separated and the aqueous layer was extracted twice with 40 ml each of benzene. The resultant aqueous layer was used again in the subsequent run as an aqueous palladium acetate solution. The yields of the acetone-azine thus obtained are shown below.

| Run No. | Yield of Acetone-Azine (%) |
|---|---|
| 1 | 60.5 |
| 2 | 64.0 |
| 3 | 60.4 |
| 4 | 67.3 |
| 5 | 66.5 |

PREPARATION OF HYDRAZINE

The acetone-azine obtained was separated from the combined benzene layers by distillation and 35% by weight of the aqueous acetone-azine solution was prepared. 14.8 g of concentrated sulfuric acid was gradually added to 25 g of the aqueous acetone-azine solution, to thereby form precipitates. These precipitates were filtered, washed with a small amount of cold water and dried. Thus, 10 g of monohydrazine sulfate was obtained.

EXAMPLE 59

0.56 g of palladium acetate and 0.52 g of EDTA.4Na was dissolved in 36 g of 25% aqueous ammonia, and then, 15.8 g of acetone and 5.54 g of 30.5% aqueous hydrogen peroxide were added. Thereafter, the mixture was heated to a temperature of 70° C. and allowed to react for 10 hours. The yield of the acetone-azine thus obtained was 24.9%.

What we claim is:

1. In a process for producing a ketazine having the formula

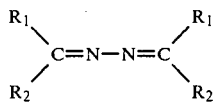

wherein $R_1$ represents alkyl group having 1 to 4 carbon atoms and $R_2$ represents (i) an alkyl group having 1 to 4 carbon atoms or (ii) phenyl or phenyl substituted by alkyl having 1 to 4 carbon atoms, alkoxy having 1 to 4 carbon atoms or halogen, and $R_1$ and $R_2$ together with the carbon atom to which they are both bonded form a ring, by reacting an aliphatic or aromatic ketone having the formula:

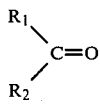

wherein $R_1$ and $R_2$ are as defined above, with ammonia and a peroxide compound or compounds, at a temperature of from 0° to 120° C., in liquid phase, the improvement wherein silica, at least one palladium compound or a mixture thereof is used as a catalyst.

2. A process as claimed in claim 1, wherein said ketone is selected from acetone, methyl ethyl ketone, methyl isobutyl ketone, cyclohexanone and acetophenone.

3. A process as claimed in claim 1, wherein said peroxide compound is hydrogen peroxide.

4. A process as claimed in claim 1, wherein said peroxide compound is selected from a liquid phase oxidation reaction product of secondary alcohol with oxygen, a reaction product of said ketone $R_1COR_2$ and hydrogen peroxide, and a reaction product of said ketone $R_1COR_2$, hydrogen peroxide and ammonia.

5. A process as claimed in claim 4, wherein said peroxide compound has the formula

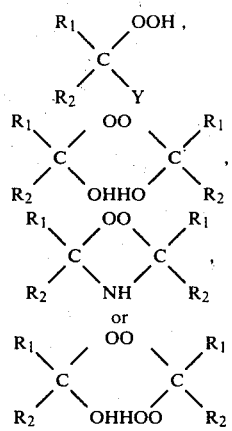

herein $R_1$ and $R_2$ are as defined above and Y represents OH or $NH_2$.

6. A process as claimed in claim 1, wherein said catalyst is amorphous silica.

7. A process as claimed in claim 6, wherein the amount of the catalyst is within the range of from 2 to 50% by weight based upon the total weight of the reaction mixture.

8. A process as claimed in claim 1, wherein said catalyst is at least one palladium (II) compound.

9. A process as claimed in claim 8, wherein the amount of the catalyst is within the range of from 0.001 to 5.0 millimol based upon 1 g of the reaction mixture.

10. A process as claimed in claim 8, wherein the palladium (II) compound is selected from palladium chloride, palladium fluoride, palladium bromide, palladium nitrate, palladium sulfate, palladium cyanide, palladium oxychloride, palladium acetate, palladium propionate, palladium oxalate, palladium dipyridyl chloride, palladium dipyridyl nitrate, sodium palladium chloride, potassium palladium chloride, palladium acetylacetonate and palladium (II)-1:4-naphthoquino-5-oleate.

* * * * *